US008560473B2

(12) United States Patent
Doerr et al.

(10) Patent No.: US 8,560,473 B2
(45) Date of Patent: Oct. 15, 2013

(54) OPERATING ABILITY MONITORING SYSTEM

(75) Inventors: Thomas Doerr, Berlin (DE); Michael Diebold, Berlin (DE)

(73) Assignee: Biotronik Se & Co. KG, Berlin (DE)

( * ) Notice: Subject to any disclaimer, the term of this patent is extended or adjusted under 35 U.S.C. 154(b) by 279 days.

(21) Appl. No.: 13/178,379

(22) Filed: Jul. 7, 2011

(65) Prior Publication Data

US 2012/0023049 A1 Jan. 26, 2012

Related U.S. Application Data

(60) Provisional application No. 61/366,177, filed on Jul. 21, 2010.

(51) Int. Cl.
*G06F 15/00* (2006.01)

(52) U.S. Cl.
USPC .......................................................... 706/20

(58) Field of Classification Search
USPC .......................................................... 706/20
See application file for complete search history.

(56) References Cited

U.S. PATENT DOCUMENTS

| | | | |
|---|---|---|---|
| 6,070,098 A | 5/2000 | Moore-Ede et al. | |
| 2004/0044293 A1 | 3/2004 | Burton | |
| 2005/0137753 A1 | 6/2005 | Basson | |
| 2005/0137755 A1 * | 6/2005 | Chase et al. | 701/1 |
| 2007/0135866 A1 * | 6/2007 | Baker et al. | 607/60 |
| 2008/0202134 A1 * | 8/2008 | Zima et al. | 62/149 |

FOREIGN PATENT DOCUMENTS

EP 1661511 5/2006

OTHER PUBLICATIONS

European Search Report dated Dec. 5, 2011. (7 pages).
Seidl et al, "Diagnostic Assessment of Recurrent Unexplained Syncope with a New Subcutaneously Implantable Loop Recorder", Europace (2000) vol. 2, pp. 256-262.

* cited by examiner

*Primary Examiner* — Kakali Chaki
*Assistant Examiner* — Michael Zidanic
(74) *Attorney, Agent, or Firm* — ARC IP Law, PC; Joesph J. Mayo

(57) ABSTRACT

An operating ability monitoring system that includes a person-dependent acceleration sensor, a telemetry unit, and an evaluation unit, wherein the person-dependent acceleration sensor and the telemetry unit may be worn by and/or implanted in a machine operator and connected to the evaluation unit, and wherein the evaluation unit is configured to receive acceleration values originating from the person-dependent acceleration sensor and sensor values originating from a further sensor that reflects the movements and/or acceleration of a vehicle or moving machine and to evaluate them by comparing the acceleration values from the person-dependent acceleration sensor to the sensor values associated with the vehicle or moving machine.

18 Claims, 6 Drawing Sheets

OPERATING ABILITY MONITORING SYSTEM

This application claims the benefit of U.S. Provisional Patent Application 61/366,177, filed 21 Jul. 2010, the specification of which is hereby incorporated herein by reference.

BACKGROUND OF THE INVENTION

1. Field of the Invention

Embodiments of the invention relate to an operating ability monitoring system for monitoring the operating ability of a vehicle driver or machine operator to operate a vehicle or the like.

2. Description of the Related Art

The driver of a vehicle as a moving machine should, to the extent possible, be able to drive—or, in more general terms, be able to operate—the vehicle so as to not pose a risk to himself or third parties. It is possible for the driver of a vehicle, just like an operator of a machine, to lose his operating ability, such as due to a dizzy spell, fatigue, or other causes.

Solutions described in the past for influencing the vehicle by electronic implants have been limited to the evaluation of rhythmological or similar physiological parameters and a direct vehicle influence derived therefrom. Frequently, however, the genesis of a temporary driving ability disorder is unknown and cannot be reliably detected by the implant indicated for the patient. A typical example is an implantable EKG recorder, which is used to diagnose syncopes. Although such a recorder would be able to detect a state of driving inability based on a cardiac rhythm analysis, it is known that more than half of syncopes are not rhythm-related [K. Seidl et al.: Initial experience with implantable loop recorders, Europace, Vol. 2, July 2000], which is to say, they have different causes and can therefore not be detected by the implants mentioned above.

BRIEF SUMMARY OF THE INVENTION

Embodiments of the invention provide an operating ability monitoring system for monitoring the operating ability of a vehicle driver or machine operator to operate a vehicle or the like. Specifically, embodiments of the invention are related to the ability of the machine operator to operate a moving machine, wherein the machine operator has a place on or in the machine, so that the operator is moved together with the machine and as a result of the machine movement is exposed to acceleration.

It is a feature of embodiments of the invention to create an operating ability monitoring system which detects states of reduced operating ability of a vehicle driver or machine operator to the extent possible. For example, the operating ability monitoring system is intended to enable a driver assistance system to derive the driving ability state of a vehicle driver or machine operator or of a patient and take it into consideration for the control of the vehicle.

According to embodiments of the invention, this is achieved by an operating ability monitoring system comprising a person-dependent acceleration sensor, a telemetry unit, and an evaluation unit, wherein the person-dependent acceleration sensor and the telemetry unit are designed to be attached to a machine operator and connected to the evaluation unit, and wherein the evaluation unit is designed to receive acceleration values originating from the person-dependent acceleration sensor and movement values originating from a further sensor that reflect the movements and/or acceleration of a vehicle or moving machine and to evaluate them by comparing the acceleration values to the evaluation values.

More specific the operating ability monitoring system comprising a person-dependent acceleration sensor, a telemetry unit, and an evaluation unit, wherein the person-dependent acceleration sensor and the telemetry unit are designed to be worn by and/or implanted in a machine operator—meaning, they are person-dependent—and connected to the evaluation unit, and wherein the evaluation unit is designed to receive acceleration values originating from the person-dependent acceleration sensor to be worn and/or implanted and movement values originating from a further sensor that reflect the movements and/or acceleration of a vehicle or moving machine and to evaluate them by comparing the acceleration values to the movement values.

The acceleration values and the movement values may be present in the form of time series or vectors, which each represent a sequence of acceleration or movement values sampled over time.

The operating ability monitoring system according to embodiments of the invention is thus in a position to detect how a vehicle driver or machine operator responds to movements of the vehicle or the machine and can derive an operating ability state therefrom.

One or more embodiment of the invention is based on the concept of making a parameter, which is independent of the actual implant diagnostics, regarding a driving ability classification from electronic implants or comparable diagnostic devices available to a driver assistance system and thus enable general information about the driving ability beyond the primary implant diagnostics.

One or more embodiments of the invention furthermore encompasses the realization that a vehicle driver or machine operator with his body muscles actively compensates for the longitudinal and transverse accelerations occurring during travel, provided he is conscious. Once this typical compensating movement is no longer present, a reduced driving ability can be assumed.

In one variant of the operating ability monitoring system, a system is provided for the communication between an electronic medical device and a vehicle system, comprising
- a personal electronic medical device having a wireless telemetry unit, and
- a telemetry unit in a vehicle for direct or indirect communication with the medical device.

To this end, the medical device comprises at least one person-dependent acceleration sensor, which detects two- or three-dimensional acceleration values of the body of the patient and makes these available to an evaluation unit, wherein the evaluation unit compares the acceleration data of the medical device to the acceleration data and driving parameters of the vehicle and, based on this comparison, derives a classification of the current driving ability state of the driver and makes it available to the driver assistance system of the vehicle as a control variable.

In general, it is assumed that the respective vehicle or a machine to be operated is provided with sensors for detecting the vehicle acceleration, yaw rates, and the like—which is to say, the movement of the machine. The movement data that is obtained from the vehicle is also referred to herein as "movement values", which may be converted into acceleration data that may be compared to the person-dependent acceleration values obtained from the person-dependent acceleration sensor for example.

According to another embodiment, the person-dependent acceleration sensor, the telemetry unit, and the evaluation unit are elements of a medical device. The telemetry unit is then designed to receive evaluation values, which originate from a machine monitoring system, and to forward them to the evaluation unit.

The operating ability monitoring system may comprise a relay station for the wireless communication between a machine monitoring system and the telemetry unit of the medical device. Because of the communication that is made possible in this way between the medical device and the vehicle by way of an interconnected relay station, which brings about an isolation between the medical device and the vehicle system, it is ensured, even in the event of a fault, that the functioning of the medical device is free from interference from the vehicle system.

In the latter case, the evaluation unit can also be an element of the relay station and receives the acceleration values wirelessly from the person-dependent acceleration sensor and the telemetry unit connected thereto. In this case, the relay station receives the evaluation values representing the movement or acceleration of the machine from the machine monitoring system.

According to a third alternative, the evaluation unit is an element of the machine monitoring system.

The evaluation unit may for example be designed to compare the acceleration values to the movement values and to derive a classification of the current operating ability state based on this comparison, and to make a result of the classification available to the machine monitoring system as a control variable.

According to another embodiment of the evaluation unit, it is designed to carry out the comparison as a parameter comparison of the acceleration values and the movement values by way of cross-correlation, variance analysis or analysis of covariance.

In addition or as an alternative, the evaluation unit may also comprise a neural network for the parameter comparison of the acceleration values to the movement values. The network can be designed to be self-learning or adaptive comprising an evaluator.

In any case, an evaluation unit which is designed to carry out an analysis for the parameter comparison for the driving ability classification may operate both in the time and in the frequency domain.

According to another embodiment of the operating ability monitoring system, the system is designed to trigger a response test in the event that the operating ability is classified as impaired. Depending on the result of the response test, the classification of the operating ability is confirmed or repealed by the evaluation unit.

The medical device may include an electronic implant or another device worn by the patient on the body, for example on the upper body.

The communication between the medical device and machine controller or relay station may take place in the MICS or ISM frequency band for example.

According to another variant, the medical device is designed to transmit at least one further physiological parameter to the evaluation unit for evaluating the operating ability.

A solution according to embodiments of the invention to the object stated above is also an evaluation unit for an operating ability monitoring system, which comprises
- an input for acceleration values representing the acceleration of a medical device,
- an input for movement values representing the movements or acceleration of a moving machine, and
- an output for the operating ability classification result.

The evaluation unit is designed to obtain a particular operating ability classification result by comparing acceleration values and movement values that are temporally associated with each other.

The evaluation unit may be designed to supply a classification result that represents a reduced operating ability when the comparison of the acceleration values to the movement values indicates that the acceleration values and the movement values agree to an extent that exceeds a predetermined threshold value. For this purpose, the evaluation unit can be designed to carry out the comparison of the acceleration values to the movement values by way of cross-correlation, a covariance analysis, a variance analysis, and/or pattern matching.

In order to achieve the object, additionally a method for classifying the operating ability of a machine operator of a moving machine is proposed, which includes the following steps:
- Providing acceleration values representing the acceleration of a medical device,
- providing movement values representing the movements or acceleration of a moving machine,
- comparing acceleration values and movement values that are temporally associated with each other, and
- classifying the operating ability as reduced if the comparison of the acceleration values to the movement values indicates that the acceleration values and the movement values agree to an extent that exceeds a predetermined threshold value.

To this end, according to another embodiment of the method the comparison of the acceleration values and movement values that are temporally associated with each other may include cross-correlation, covariance analysis, variance analysis and/or pattern matching.

BRIEF DESCRIPTION OF THE DRAWINGS

Embodiments of the invention will now be described in more detail based on exemplary embodiments with reference to the figures. The figures show.

DETAILED DESCRIPTION OF THE INVENTION

Figure 1:
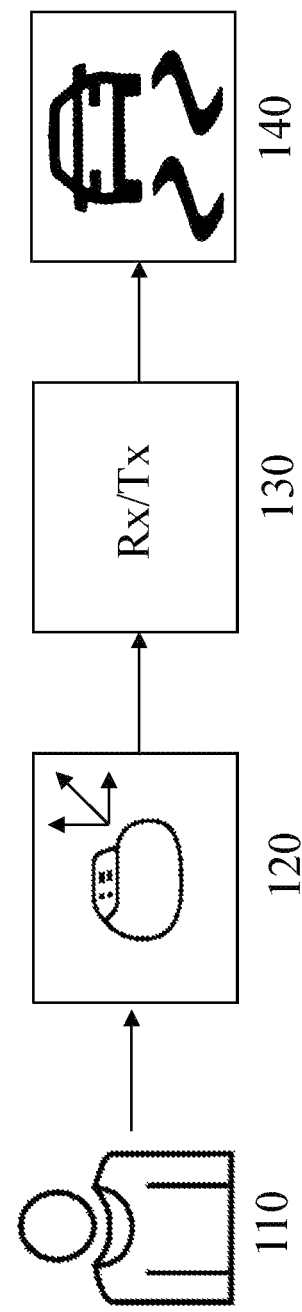
FIG. 1: the block diagram of the operating ability sensor according to embodiments of the invention.

FIG. 1 illustrates the block diagram of an operating ability monitoring system according to embodiments of the invention. The patient/driver (110), who is the machine operator, wears an electronic implant (120), such as a cardiac pacemaker, defibrillator or loop recorder. By way of a person-dependent 3D acceleration sensor coupled with the electronic implant, (or other device as per FIG. 4), this electronic implant (120) continuously detects the acceleration values occurring in for example the upper body of the patient/driver, and transmits this information to a relay station (130) on a regular basis by way of an MICS frequency band transmission protocol. The relay station (130) in turn is queried on a regular basis by a driver assistance system (140) as the machine monitoring system. The driver assistance system then compares the acceleration data made available to the driver assistance system (140) to the acceleration information of the vehicle and derives a classification of the driver ability therefrom.

Figure 2:
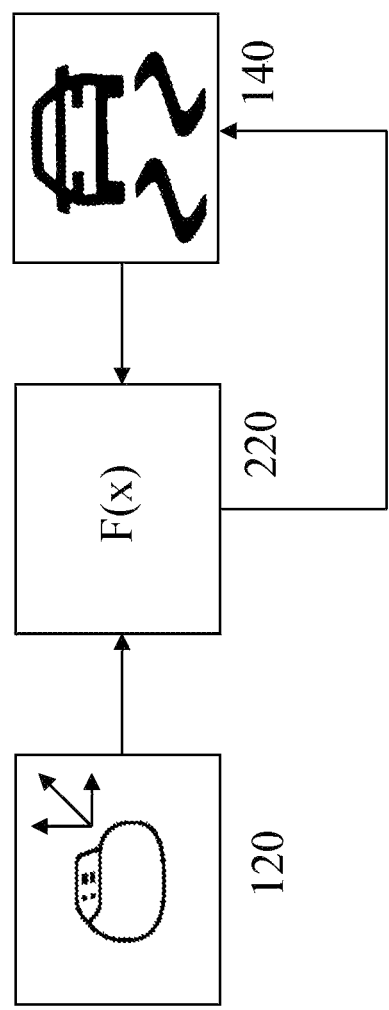
FIG. 2: an evaluation unit of the operating ability monitoring system according to embodiments of the invention and the interfaces thereof.

FIG. 2 illustrates the evaluation unit (220) and the interfaces thereof. Both the electronic implant (120) and the driver assistance system (140) send standardized acceleration data in the form of acceleration vectors to the evaluation unit (220). Evaluation unit (220) may reside in any electronic component within the system, for example in any component configured with a computing device. This unit then determines the relationship of these acceleration vectors and based thereon classifies an assumed driving ability state and signals the same to the driver assistance system (140). If a reduction in the driving ability is detected, a response test may in one or more embodiments, be required from the driver/patient by the driver assistance system as a plausibility check. The driver, for example, has to respond within a defined period to an optical, acoustic or similar signal. If this response does not take place, the driver assistance system assumes driving inability and initiates a corresponding response.

The results of the response test can additionally be used as an evaluation variable for a self-learning evaluation unit (220), such as when the evaluation unit comprises a neural network, which is self-learning comprising an evaluator. The results of the response test are then made available to the evaluator of the neural network.

Figure 3:
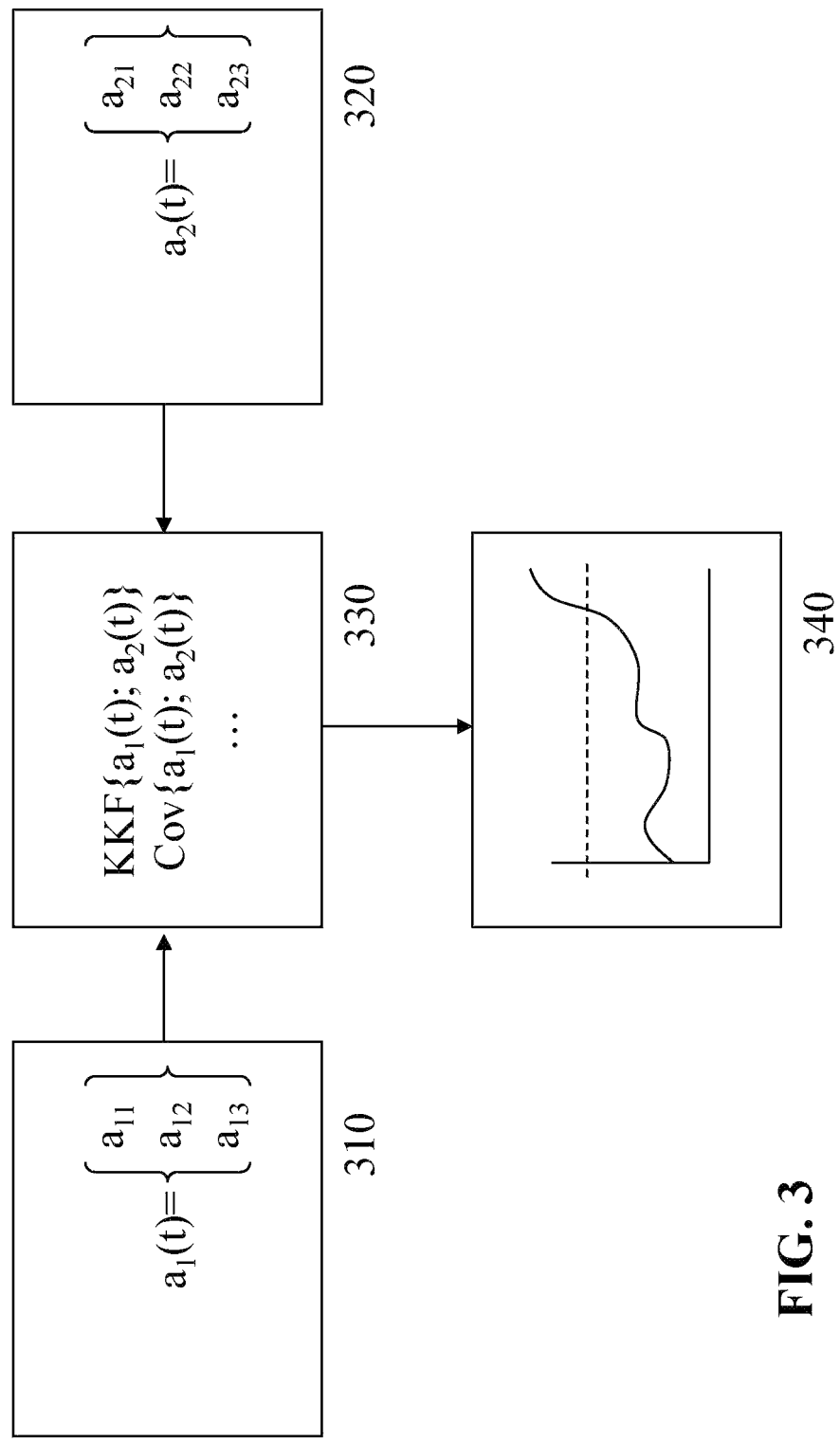
FIG. 3: an example of a comparison of the movement and acceleration information in the evaluation unit.

FIG. 3 illustrates the comparison of the acceleration information by the evaluation unit. The input variables used are the standardized acceleration vectors of the medical device (310)—these being the acceleration values—and the standardized acceleration vectors of the driver assistance system (320), these being the movement values, which again are vehicle related acceleration values. These are compared to each other by using one or more of the following methods (330):

Cross-correlation (KKF)
Covariance analysis (Cov)
Variance analysis
Pattern matching (such as pattern matching in the neural network).

The evaluation unit can carry out the comparison both in the time and the frequency domain.

If the difference of the two compared vectors (340) exceeds a threshold value, driving inability is assumed, because in this case the acceleration data of the patient is directly dependent on the vehicle acceleration data, thereby allowing the assumption that the normally present compensating muscle activities of the patient are reduced or do not take place at all during travel.

Figure 4:
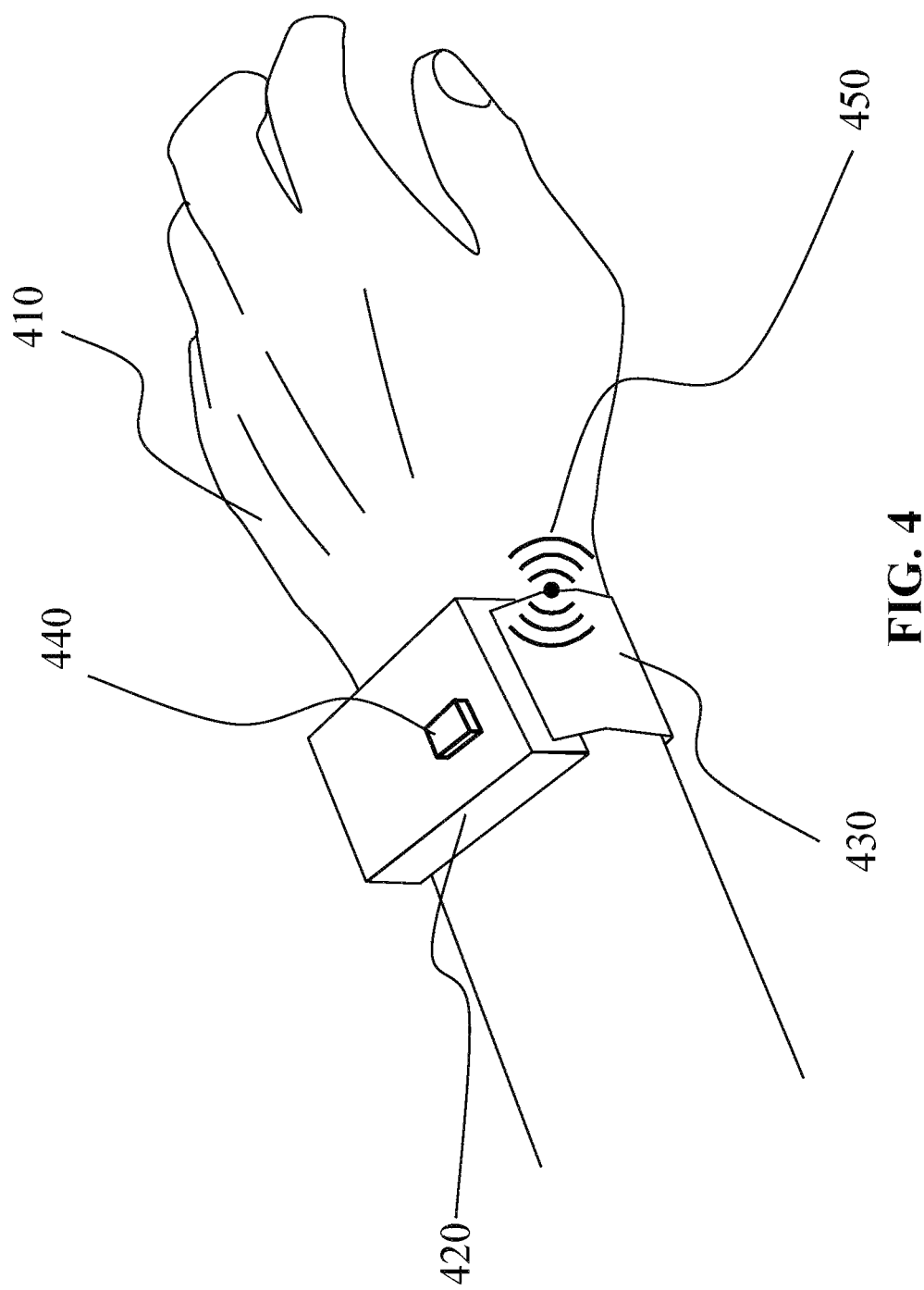
FIG. 4: an exemplary embodiment of the person-dependent components of the operating ability monitoring system according to embodiments of the invention.

FIG. 4 illustrates another embodiment of the person-dependent acceleration sensor. Here, the acceleration information is detected at the wrist (410) of the patient by way of what is referred to as a CardioWatch (420). It comprises a person-dependent 3D acceleration sensor (440) and, at the same time, is used as the relay station (450) for RF data transmission between the person-dependent acceleration sensor and the vehicle system. The antennas required for telemetry may be integrated in the wristband (430) of the CardioWatch for example.

Below, a possible implementation of the classification of the operating ability by the evaluation unit is explained, using cross-correlation.

The input variables for the operating ability classification used by the evaluation unit are the time series of the previously standardized acceleration vectors of the person-dependent acceleration sensor as for example implemented inside an electronic implant $x(t)=\{x1(t), x2(t), x3(t)\}$ and the time series of the standardized acceleration vectors of the vehicle $y(t)=\{y1(t), y2(t), y3(t)\}$.

Because the position and/or orientation of the person-dependent acceleration sensor present in the electronic implant are dependent on the implantation position, the evaluation unit first calculates a rough allocation to the unit vectors of the vehicle system. For this purpose, for each vector combination the cross-correlation function is calculated according to:

$$R_{xy}(\tau) = \lim_{T_F \to \infty} \frac{1}{T_F} \int_{-T_F/2}^{T_F/2} x(t) \cdot y(t+\tau) \, dt$$

which is to say:

Rx1y1; Rx1y2; Rx1y3; Rx2y2; Rx2y3 and Rx3y3.

$\tau$ is selected, while taking the sampling frequency into consideration, such that the cross-correlation function can be determined for windows lasting a predefined time, for example at least 2 seconds in one embodiment, so that the maximum assumed phase shift between the acceleration of the vehicle and of the implant/patient is detected.

Figure 5:
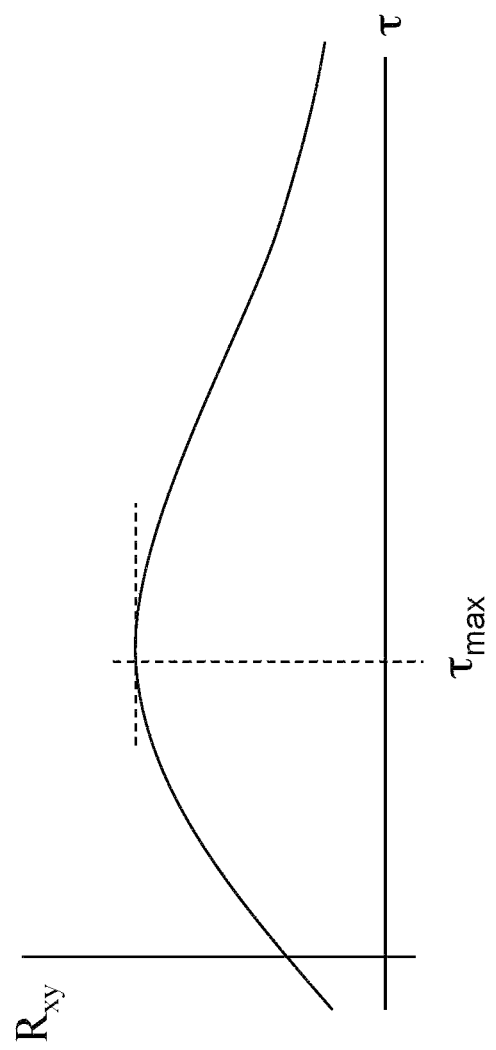
FIG. 5: illustrates determination of the maximum value of the cross-correlation function $R_{xy}(\tau)$, i.e., at the value of $\tau$ where the maximum value of $R_{xy}(\tau)$ occurs, namely $\tau_{max}$.

For the cross-correlation functions $R_{xy}(\tau)$ determined in the step described immediately above, the evaluation unit now determines $\tau$ for the maximum value $\tau_{max}$, which is shown in FIG. 5, and which corresponds to the phase value $\tau$ where the maximum value occurs.

Figure 6:
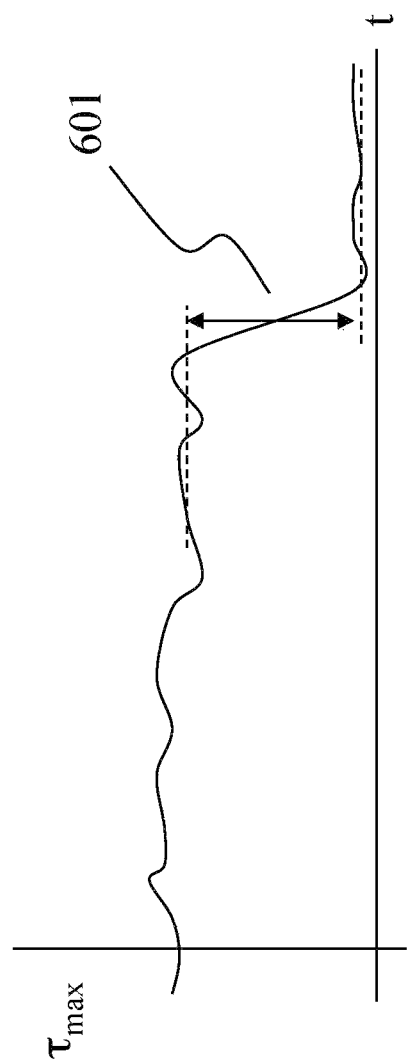
FIG. 6: illustrates the temporal curve of $\tau_{max}$ that is recorded and analyzed over time and further shows a sudden and lasting change that takes place and which is shown as a change or drop over a threshold.

In order to determine the evaluator signal for the classification of the driving ability state, the temporal curve of $\tau_{max}$ is recorded for all of the above correlation functions in the trends and analyzed. The analysis includes in particular discontinuity and stability criteria. If, for example, a sudden and lasting change takes place of $\tau_{max}$ in X from Y correlation functions, a driving inability must be suspected and reported to the driver assistance system. This for example is shown as a change or drop over a threshold 601 in $\tau_{max}$ as shown in FIG. 6.

The entire calculation/evaluation may be carried out on a regular basis so that a complete calculation and evaluation takes place repeatedly, for example in one embodiment, at least every 0.1 sec.

If such a suspected case of reduced driving ability occurs, the driver is first requested to perform a "response test". If the required response does not take place within a period, such as 2 sec, or depending on the speed or route, the driving ability is considered to be definitely reduced, and the driver assistance system actively may intervene in the course of travel.

The solution according to embodiments of the invention offers the advantage that an evaluation of a driving ability state can be easily and robustly implemented by the driver assistance system for wearers of electronic medical devices/implants. The advantage of the solution according to embodiments of the invention is in particular that this classification takes place independently of the actual implant diagnostics, whereby it is also possible to detect states of driving inability, which have causes that are independent of the indication of the medical device.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An operating ability monitoring system comprising:
a person-dependent acceleration sensor configured to couple with a machine operator;
a telemetry unit coupled with said person-dependent acceleration sensor;
a second sensor coupled with a vehicle or moving machine operated by said machine operator;
an evaluation unit configured to
receive acceleration values from the person-dependent acceleration sensor and,
receive movement values from the second sensor coupled with said vehicle or said moving machine which represent acceleration of said vehicle or said moving machine and,
compare the acceleration values from the person-dependent acceleration sensor to the acceleration values from the second sensor coupled with the vehicle or the moving machine and,
derive a classification of a current operating ability state based on said compare;
a machine monitoring system;
wherein the evaluation unit is further configured to make a result of the classification of the current operating ability state available to the machine monitoring system;
wherein the evaluation unit is further configured to trigger a response test in the event that the current operating ability state is classified as impaired, wherein the evaluation unit is further configured, depending on the response test, to confirm or repeal the classification of the current operating ability state; and
wherein said response test is a plausibility check enabling said driver to respond to said response test within a defined period to detect a reduction in the driving ability such that if a response from the driver does not take place, the machine monitoring system assumes driving inability and initiates a corresponding response of intervening in a course of travel associated with the driver.

2. The operating ability monitoring system according to claim 1, wherein the person-dependent acceleration sensor and the telemetry unit are configured to be worn by and/or implanted in said machine operator.

3. The operating ability monitoring system according to claim 1, wherein the person-dependent acceleration sensor, the telemetry unit, and the evaluation unit are elements of a medical device associated with said machine operator, wherein the telemetry unit is configured to receive acceleration values from said second sensor, and wherein said second sensor is associated with said machine monitoring system.

4. The operating ability monitoring system according to claim 3, wherein the operating ability monitoring system further comprises a relay station configured to wirelessly communicate between said machine monitoring system and the telemetry unit of the medical device, wherein the relay station ensures, even in the event of a fault, that the functioning of the medical device is free from interference from the machine monitoring system.

5. The operating ability monitoring system according to claim 4, wherein the evaluation unit is an element of the relay station and is configured to receive the acceleration values wirelessly from the person-dependent accelerator sensor via the telemetry unit connected thereto and to receive the movement values that represent the acceleration of the vehicle from the machine monitoring system.

6. The operating ability monitoring system according to claim 3, wherein the evaluation unit is an element of the machine monitoring system.

7. The operating ability monitoring system according to claim 1, wherein said compare comprises a cross-correlation, variance analysis or analysis of covariance.

8. The operating ability monitoring system according to claim 1, wherein said compare utilizes a neural network.

9. The operating ability monitoring system according to claim 1, wherein said compare is implemented in both time and frequency domains.

10. An operating ability monitoring system comprising:
an evaluation unit configured to
receive acceleration values from a person-dependent acceleration sensor and
receive movement values from a second sensor coupled with a vehicle or a moving machine which represent acceleration of said vehicle or said moving machine and
compare the acceleration values from the person-dependent acceleration sensor to the acceleration values from the second sensor coupled with the vehicle or the moving machine and
derive a classification of a current operating ability state based on said compare; and
a machine monitoring system;
wherein the evaluation unit is further configured to make a result of the classification of the current operating ability state available to the machine monitoring system;
wherein the evaluation unit is further configured to trigger a response test in the event that the current operating ability state is classified as impaired, wherein the evaluation unit is further configured, depending on the response test, to confirm or repeal the classification of the current operating ability state; and
wherein said response test is a plausibility check enabling said driver to respond to said response test within a defined period to detect a reduction in the driving ability such that if a response from the driver does not take place the machine monitoring system assumes driving inability and initiates a corresponding response of intervening in a course of travel associated with the driver.

11. The operating ability monitoring system according to claim 10, wherein the evaluation unit is further configured to supply the operating ability classification result that represents a reduced operating ability when said compare of the acceleration values to the movement values indicates that the acceleration values and the movement values differ to an extent that exceeds a predetermined threshold value.

12. The operating ability monitoring system according to claim 10, wherein said compare comprises cross-correlation, covariance analysis, variance analysis, and/or pattern matching.

13. The operating ability monitoring system according to claim 10, wherein said compare comprises utilizing a neural network.

14. The operating ability monitoring system according to claim 10, further comprising a medical device wherein said evaluation unit is implemented in said medical device.

15. The operating ability monitoring system according to claim 10, wherein said evaluation unit is implemented in said machine monitoring system.

16. The operating ability monitoring system according to claim 10, further comprising a relay station wherein said evaluation unit is implemented in said relay station.

17. A method for classifying the operating ability of a machine operator of a moving machine, comprising:
- receiving acceleration values from a person-dependent acceleration sensor;
- receiving movement values from a second sensor coupled with a vehicle or a moving machine which represent acceleration of said vehicle or said moving machine;
- comparing the acceleration values from the person-dependent acceleration sensor to the acceleration values from the second sensor coupled with the vehicle or the moving machine;
- deriving a classification of a current operating ability state based on said comparing;
- supplying the result of the classification of the current operating ability state;
- triggering a response test in the event that the current operating ability state is classified as impaired, wherein depending on the response test, confirming or repealing classification of the current operating ability state; and
- wherein said response test is a plausibility check enabling a driver to respond to said response test within a defined period to detect a reduction in the driving ability, and
- wherein when a response from the driver does not take place, assuming driving inability and initiating a corresponding response of intervening in a course of travel associated with the driver.

18. The method according to claim 17, wherein said comparing of the acceleration values and sensor values that are temporally associated with each other includes cross-correlation, covariance analysis, variance analysis and/or pattern matching or utilizing a neural network.

* * * * *